United States Patent [19]

Goldberg et al.

[11] Patent Number: 5,194,262

[45] Date of Patent: Mar. 16, 1993

[54] ENCAPSULATED ANTIPERSPIRANT SALTS AND DEODORANT/ANTIPERSPIRANTS

[75] Inventors: Marvin E. Goldberg, Marlboro, N.J.; David M. Kellner, Hollis, N.Y.; Chel W. Lew; Cathy S. Lamb, both of San Antonio, Tex.

[73] Assignee: Revlon Consumer Products Corporation, New York, N.Y.

[21] Appl. No.: 740,831

[22] Filed: Aug. 6, 1991

Related U.S. Application Data

[63] Continuation-in-part of Ser. No. 601,440, Oct. 22, 1990, abandoned.

[51] Int. Cl.⁵ .......................... A61K 7/32; A61K 9/50
[52] U.S. Cl. ..................................... 424/401; 424/65; 424/66; 424/68; 424/DIG. 5; 424/489; 424/47
[58] Field of Search ................. 424/65, 66, 68, 47, 424/DIG. 5, 401, 489

[56] References Cited

U.S. PATENT DOCUMENTS

| | | | |
|---|---|---|---|
| 3,091,567 | 5/1963 | Wurzberg | 424/418 |
| 3,565,559 | 2/1971 | Sato | 424/492 |
| 3,686,701 | 8/1972 | Charle | 424/61 |
| 3,691,271 | 9/1972 | Charle | 424/431 |
| 3,971,852 | 1/1976 | Brenner | 426/103 |
| 4,123,382 | 10/1978 | Morse | 427/213.32 |
| 4,308,165 | 12/1981 | Vassiliades | 428/402.21 |
| 4,369,173 | 1/1983 | Causland et al. | 424/47 |
| 4,605,554 | 8/1986 | Prussin et al. | 424/65 |
| 4,724,240 | 2/1988 | Abrutyn | 424/DIG. 5 |
| 4,795,436 | 1/1989 | Robinson | 424/422 |
| 4,803,195 | 2/1989 | Holzer | 514/4 |
| 4,818,522 | 4/1989 | Ferentchek | 424/66 |
| 4,855,127 | 8/1989 | Abrutyn | 514/847 |
| 4,882,166 | 11/1989 | Graham | 424/462 |
| 4,976,961 | 12/1990 | Norbury | 424/401 |
| 5,013,473 | 5/1991 | Norbury | 424/65 |
| 5,039,518 | 8/1991 | Barone | 424/63 |

FOREIGN PATENT DOCUMENTS 2723682 10/1976 Fed. Rep. of Germany .
2486396 7/1980 France .

OTHER PUBLICATIONS

Chem Abstracts 113(24):217799d Dec. 10, 1990 Kirk-Othmer-Encyclopedia of Chemical Technology, 3rd Ed., vol. 15, 470–493 (1981).
Pharmaceutical Formulas, 1946.

Primary Examiner—Thurman K. Page
Assistant Examiner—Amy Hulina
Attorney, Agent, or Firm—Julie Blackburn

[57] ABSTRACT

Microencapsulates containing antiperspirant salts, microencapsulates in conjunction with bioadhesives, and antiperspirant/deodorant compositions containing the microencapsulates of the invention.

31 Claims, No Drawings

ENCAPSULATED ANTIPERSPIRANT SALTS AND DEODORANT/ANTIPERSPIRANTS

This application is a continuation in part of copending application Ser. No. 07/601,440, filed Oct. 22, 1990, now abandoned.

TECHNICAL FIELD

The invention is in the field of microencapsulates containing antiperspirant salts therein, and antiperspirants and deodorants containing these microencapsulates.

BACKGROUND OF THE INVENTION

Deodorants are preparations which have antimicrobial activity and which mask, remove, or decrease perspiration odor. Antiperspirants are substances which have astringent action and inhibit the flow of perspiration. Salts of metals such as aluminum, zirconium, zinc, etc. have astringent properties and are often used in antiperspirants. When these salts are mixed into standard vehicles and applied to the skin, perspiration flow is inhibited as long as the antiperspirant salts remain on the applied area. However, the length of time an antiperspirant is effective depends largely on how profusely an individual sweats. The excretion of sweat tends to wash away the antiperspirant salts and thus reduce the effectiveness of an antiperspirant formulation. Obviously the rate at which antiperspirant salts wash away correlates directly with the degree to which an individual sweats.

Thus a means of providing more effective, longer lasting antiperspirants is definitely of interest.

Microencapsulation is a process by which a given substance or material is protected or separated from its surrounding environment in a protective covering. Microencapsulation of certain core materials is often desired to facilitate controlled release of the microcapsule contents into a specified environment. Time release microcapsules release their core materials at a controlled rate. The result is that the core material has a longer effective life since it is released from protective microcapsules at different times. The benefits of controlled release are obvious. For example, when pharmaceuticals are in the controlled release format, it generally allows the user to ingest or apply one long acting dose of drug instead of being obliged to ingest or apply many small doses of drug throughout a time period.

The microencapsulation of fragrances, inks, and a myriad of other substances is known in the art. Fragrance microcapsules are often found in scratch and sniff inserts in magazines, in perfumes, deodorants, and host of other applications.

There are many obvious advantages in microencapsulating antiperspirant salts. Antiperspirant salts sometimes cause skin irritation in sensitive individuals. Since the internal constituents of microcapsules are insulated from the surrounding environment (i.e. skin), and released only when needed, skin irritation may be substantially alleviated in susceptible individuals. Microencapsulation of antiperspirant salts also provides for controlled release of the internal constituents, hence lengthening the effective period of the antiperspirant. However, antiperspirant salts are difficult to encapsulate due to their acidic nature. Up until now it has been found that most antiperspirant salts rapidly degrade or react with the substances used to form the outer shell of the microcapsule. Microcapsules can also be washed away by sweating just as antiperspirants salts, so a means of keeping the microcapsule securely anchored to skin is also desireable.

SUMMARY OF THE INVENTION

The invention is directed to microencapsulates containing antiperspirant salts therein.

The invention is directed to microencapsulates containing therein antiperspirant salts, in conjunction with a bioadhesive which anchors the microencapsulate to the skin.

The invention is directed to antiperspirant/deodorant compositions containing the microencapsulates of the invention.

The invention is directed to a method for making the microcapsules of the invention.

DETAILED DESCRIPTION

The term "microencapsulate", or "microcapsule" means a core material, particularly one or more antiperspirant salts, which is secluded or protected from the surrounding environment by a protective coating or shell which subsequently releases the antiperspirant salts in response to certain stimuli.

The term "bioadhesive" means a biological or chemical substance or molecule capable of adhering to a biological surface and which may remain fixed at a certain site in or on the human body (i.e. epithelium) for a certain period of time. Bioadhesion occurs due to a molecular force across the interface between the biological surface (i.e. epithelium) and a polymeric material with bioadhesive properties, which interface resists interfacial separation. In the case of the invention, the microcapsule either contains a bioadhesive within its outer shell, or the bioadhesive is coated onto the outer shell of the microcapsule. The bioadhesive acts to bond or secure the microcapsule to the skin for a certain period of time. The microcapsule constitutents are subsequently released in response to certain stimuli The invention encompasses the discovery that the following shell wall materials may be used for the microcapsule when antiperspirant salts are used as the core materials. Suitable shell wall materials in accordance with the invention include the waxes, lipids or oils, or polymers, or gums such as polyvinylpyrrolidone, acrylic acid resin, chitosan glutamate, cellulose, dextran, modified food starch, polyvinylalcohol, glycerin, sorbitol, maltodextrin, corn syrup solids, sodium alginate, carrageenan, xanthan gum, ozokerite wax, polyethylene oxide, agarose, ethylene vinyl acetate copolymer, polyvinylidene chloride, methyl cellulose, ethylcellulose, hydroxypropylcellulose, hydroxypropylmethylcellulose, hydroxypropylmethylcellulose phthalate, methyl cellulose, polyvinyl chloride, polystyrene, partially hydrogenated soybean oil, cottonseed oil, hydrogenated vegetable oil, microcrystalline wax, beeswax, polyethylene, shellac wax, and paraffin, natural waxes, synthetic waxes, and other gums.

The microcapsules may be made by methods well known in the art, including the atomizing nozzle or rotating disk method. In the atomizing nozzle method (which is also called spray drying or spray congealing), the antiperspirant salts are dissolved or dispersed in the shell wall solution. The solution is fed into the atomizing nozzle located in the center of a drying chamber. The solution is atomized or sprayed into small droplets and dried by a heated air stream. The rotating disc method is especially suitable for lipid type shell wall materials. In this method the antiperspirant salt is suspended in the molten material and poured into the center of a rotating disc. The liquid droplets formed at the disc periphery are solidified by cooling.

The microencapsulation methods of U.S. Pat. No.'s 3,971,853, 3,091,567, and 3,565,559 and Kirk-Othmer Encyclopedia of Chemical Technology, Third Edition, Vol. 15, pages 470-493 (1981) are also suitable for making the microcapsules of the invention and these publications are hereby incorporated by reference.

The microcapsules are generally made by mixing from about 1-40% of the desired shell wall material with about 60-99% of an appropriate solvent material such as water, ethanol, acetone, methanol, dichloromethane, or other similar solvents. Then the desired amount of antiperspirant salt is added to this mixture. The desired amount of salt is that amount which results in a final concentration of up to 50% antiperspirant salt and the remainder dried shell wall or microcapsule constituents in the final, dried microencapsulate. The salt may be added in any form including solution, solid, or suspension, and the amount of antiperspirant salt added depends on the form which is added to the shell wall solution. The amount of solution or suspension added depends upon the concentration of salt in the solution or suspension.

If the outer shell material is a wax or a lipid material, approximately 10-50% of antiperspirant salt may be encapsulated in about 50-90% of a suitable wax shell wall material by emulsifying the antiperspirant salt in the molten wax or lipid material. The resulting shell wall solution is then subjected to the usual microencapsulation methods, preferably rotating disk.

Mixtures of waxes, lipids, polymers and gums may be used to make the shell wall. Such suitable formulations include a composition comprising about 30-75% wax, about 10-50% antiperspirant salt, and about 1-20% of the non-wax, non-lipid shell wall materials such as Polymers or gums.

Chart I illustrates the amount of unencapsulated antiperspirant salt, encapsulated antiperspirant salt, shell wall and bioadhesive, in some typical antiperspirant formulations in accordance with the invention.

Antiperspirant salts suitable for use in the invention include those known to be used for this purpose such as aluminum bromohydrate, aluminum chlorhydrates, aluminum chlorhydrex propylene glycol (PG), aluminum dichlorohydrex PG, aluminum sesquichlorohydrex PG, aluminum chlorhydrex polyethylene glycol ,PEG), aluminum dichlorohydrex PEG, aluminum sesquichlorohydrex PEG, aluminum chloride, aluminum sulfate, aluminum zirconium chlorohydrates, aluminum zirconium trichlorohydrate, aluminum zirconium tetrachlorohydrate, aluminum zirconium pentachlorohydrate, aluminum zirconium octachlorohydrate, aluminum zirconium trichlorohydrex Gly, aluminum zirconium tetrachlorohydrex Gly, aluminum zirconium pentachlorohydrex Gly, aluminum zirconium octachlorohydrex Gly, buffered aluminum sulfate, potassium alum, sodium aluminum chlorohydroxy lactate, aluminum sesquichlorohydrates, sodium aluminum lactate, etc.

The shell wall solution is then subjected to any of the above mentioned microencapsulation methods, preferably spray drying or rotating disk. The resulting microcapsules contain the antiperspirant salts of the invention in the appropriate concentration and preferably range in size from 1-75 micrometers with 10-0 micrometers preferred. Microencapsulates made of the shell wall materials disclosed herein slowly release their internal contents by osmosis, water solubility of the shell, enzymatic degradation of the shell wall, or electrolytic means. Osmotic degradation is caused by seepage of the antiperspirant salts through the shell wall material due to osmosis. Enzymatic degradation is caused by certain enzymes found on the skin which promote degradation of the shell wall and release of the salts. Electrolytic degradation of the shell wall is caused by the difference in electrolyte balance or concentration between human skin and the microcapsule material. In some instances the shell wall materials exhibit water solubility such that the presence of water (perspiration) will cause degradation of the shell material. Heat, pressure, friction, and the presence of water all contribute to inducing the osmosis, enzymatic degradation and electrolytic degradation of the shell wall

CHART I

| | 1 | 2 | 3 | 4 | 5 | 6 | 7 | 8 | 9 | 10 |
|---|---|---|---|---|---|---|---|---|---|---|
| UNENCAPSULATED SALT* | | | | | | | | | | |
| Al Chloride | | 10 | | | 10 | | | | 10 | 10 |
| Al Chlorohydrate | | | | 10 | 5 | | 10 | | | |
| Al/Zr[1] tetrachlorhydrex gly | | 10 | | | | | 10 | | | |
| Al/Zr trichlorhydrex gly | | | | 10 | | | | 10 | | |
| ENCAPSULATED SALT* | | | | | | | | | | |
| Al Chloride | | | | | 10 | 3 | | | 5 | 5 |
| Al Chlorohydrate | | 15 | | | | 1.6 | | | | |
| Al/Zr Tetrachlorohydrex gly | 12 | | 10 | | | | 10 | | | |
| Al/Zr Trichlorohydrex gly | | | | 10 | | | 10 | | | |
| SHELL WALL* | | | | | | | | | | |
| Polyethylene | 36 | 30 | 20 | 19.6 | 27 | 15 | 27 | 27 | 30 | 27 |
| BIOADHESIVE* | | | | | | | | | | |
| Polyvinyl alcohol | | | | .4 | 3 | | | 3 | 3 | 3 |
| ANTIPERSPIRANT VEHICLE | 52 | 45 | 60 | 60 | 50 | 65.4 | 50 | 50 | 52 | 58 |

*Although specific examples of unencapsulated salt, encapsulated salt, shell wall material, and bioadhesive are given in each category, any other equivalents mentioned in the specification would be suitable.
[1]Al = Aluminum, Al/Zr = Aluminum/Zirconium The microencapsulates of the invention may be incorporated into the appropriate antiperspirant/deodorant vehicles with or without the presence of a bioadhesive, although it is preferred that a bioadhesive be used.

Suitable bioadhesive materials in accordance with the invention include sodium carboxymethyl cellulose, polyacrylic acid, tragacanth, polymethyl vinyl ether/maleic anhydride copolymer, polyethylene oxide, methylcellulose, karya gum, methylethylcellulose, soluble starch, gelatin, pectin, polyvinyl pyrrolidone, polyethylene glycol, polyvinyl alcohol, polyhydroxymethacrylate, hydroxypropyl cellulose, carbomers, and biological materials such as various animal or vegetable proteins, for example chitin, etc. The bioadhesive must be compatible with water and cannot cause premature decomposition of the microencapsulate.

The bioadhesive can be attached to the microencapsulate by simply coating the microencapsulate with the bioadhesive material. About 1-30% bioadhesive is dissolved in 60-95% solvent. The miorocapsules are dispersed in the solution and spray dried or introduced into a rotating disk.

In some cases the bioadhesive may be added directly to the shell wall solution and in the process of microencapsulation will become a part of the dried shell wall of the final microencapsulate. If incorporating the bioadhesive into the shell wall is desired, generally about 1–20% bioadhesive and about 1–40% antiperspirant salt are emulsified into about 50–95% shell wall material, which is preferably a wax or lipid material. Microcapsules are made from this solution in the usual manner.

The microencapsulate or microencapsulate/bioadhesive complex is then incorporated into a suitable vehicle for an antiperspirant/deodorant. The microcapsules alone may be incorporated into the vehicle in order to achieve the antiperspirant action, or a combination of free antiperspirant salt and microcapsules may be used. A combination is generally preferred since the free antiperspirant salts will act immediately to curb perspiration and the microcapsules will slowly release their contents over time. Any ratio of microcapsules to free antiperspirant salt is suitable so long as the antiperspirant salt concentration in the final formulation is less than 30%. Suitable vehicles include solid stick, aerosol, pump spray, roll-on, cream, lotion, gel, or Powder. In addition the microcapsules may be incorporated into pads or sponges. Generally antiperspirant/deodorant formulations in accordance with the invention may contain:

1–50% unencapsulated salt,
1–50% encapsulated salt,
10–70% shell material,
20–80% antiperspirant vehicle.

The above formulation may further comprise 0.01–30% bioadhesive which is either incorporated into the shell wall or coated onto the shell wall.

Conventional solid sticks generally comprise a wax base into which the antiperspirant salts are incorporated. A suitable wax base generally comprises one or more waxes, and if desired a number of nonessential constituents such as suspending agents, whitening agents, payoff enhancers, absorbants, wetting agents, and so on.

Roll-ons and lotions are liquid based with various possible liquids serving as the vehicle Silicones, glycols, emollients, and so on represent some of the suitable vehicles. A number of nonessential constituents such as suspending agents, drying agents, emollients, etc. may be added to enhance cosmetic effect.

In antiperspirant creams the vehicle is a cream. Generally creams contain oils and light waxes to provide the cream effect. It may also be desired to add constituents such as suspending agents, silicones, alcohol, whitening agents, and so forth.

Antiperspirant powders are powder based. The vehicle comprises powder constituents such as talc, kaolin, and other similar materials.

A cosmetically effective amount of the microcapsules in accordance with the invention ranges from about 0.01–40% with 1–30% preferred and 5.0–20% most preferred in an antiperspirant vehicle. As mentioned previously, both free antiperspirant salts and microcapsules may be incorporated into the vehicle and the ratio is a matter of preference.

Preferably the microcapsules of the invention are incorporated into a solid or roll-on type antiperspirant/deodorant.

One of the preferred embodiments of the invention is a solid stick antiperspirant comprising 0.05–30% antiperspirant salt which salt component is comprised of 0.05–5% microcapsules with the remainder of the salt component unencapsulated antiperspirant salt, 12–30% waxes, 10–70% silicone, the waxes and silicone being present by weight of the total composition. The formulation may optionally contain one or more of a suspending agent, a whitening agent, an absorbant, a wetting agent, a preservative, or mixtures thereof.

Suitable silicones include polydimethylsiloxane, phenyl dimethicone, dimethicone, cyclomethicone, hexamethylsiloxane, amodimethicone, trimethylsiloxysilicate, simethicone, stearoxytrimethylsiloxysilicate, cetyl dimethicone copolyol, and so on. The silicone components provide a pleasant layer on the skin which enhances feel.

Suitable antiperspirant salts are as mentioned previously. A wide variety of waxes may be used, their function to form a base or stick structure. Many sticks have a main wax component which is the basic stick former and one or more subordinate waxes which assist in maintaining stick structure. The alcohol waxes which are solids such as stearyl alcohol, myristal alcohol, cetyl alcohol, or tridecyl alcohols, serve as excellent main wax components. Other waxes and/or other ingredients such as microcrystalline, lanolin, paraffin, ozokerite, lanolin alcohol, hydrogenated lanolin, candelilla, cocoa butter, petrolatum, shellac wax, hydrogenated castor oil, spermaceti, bran wax, capok wax, or bayberry wax may be used as subordinate waxes.

In the preferred embodiment it is desireable to include one or more of a suspending agent, a whitening agent, a preservative, an absorbant, or a wetting agent A suspending agent aids in the suspension of the microcapsules and the antiperspirant salts in the composition as it is being poured or molded. Suitable suspending agents include silica, magnesium silicate, aluminum silicate, veegum, kaolin, clays such as quaternium 18 hectorite, etc. If a suspending agent is added, generally 0.025–10% is suggested.

A whitening agent provides a more commercially pleasant whiteness to the stick. Suitable whitening agents include such colorants as titanium dioxide, talc, mica, silicates, zinc oxide, etc. If a whitening agent is included, generally 0.1–3.0% is suggested.

It may also be desired to add preservatives to the final commercial formulation to protect against degradation of the product if it happens to have a longer than usual shelf life. Suitable preservatives include those commonly used in cosmetics such as the parabens (methyl, ethyl, propyl, butyl, etc.), imidazolidinyl urea, quaternium-15, benzyl alcohol, phenoxyethanol, to name only a few. If a preservative is added, generally 0.01–0.60% is suggested.

It may also be desired to add an absorbant to the formulation. An absorbant acts to absorb grease and oil thereby enhancing the beneficial effects of the composition. Suitable absorbants include talc or other powder type constituents such as mica, starch, silicates, clays, zinc oxide, aluminum hydroxide and so on. If an absorbant is added 0.5–8% is suggested.

A wetting agent or emulsifer is desireable. Its function is to cause the underarm sweat to easily form contact with the antiperspirant salts which are free in the formulation. A wide variety of emulsifiers are suitable including Polyethylene Glycol (PEG) 8 distearate, PEG caprylate, PEG (5-15) cocoate, PEG (4-150) dilaurate, PEG 2 dioctanoate, PEG (4-15) dioleate, PEG 3 dipalmitate, PEG (2-175) distearate, PEG (8-12) ditallate, PEG (6-12,) distearate, glycols, and so on. The numbers in parentheses indicate the number of ethylene glycol units i.e. PEG 8 distearate is polyethylene glycol distearate with 8 ethylene glycol units. The range in parentheses indicates the range of ethylene glycol units.

One preferred embodiment of the invention is where microcapsules are incorporated into a solid antiperspirant/ deodorant comprising:
10-70% silicone
0.1-3.0% titanium dioxide (whitening agent)
0.025-10% silica (suspending agent)
0.5-3% talc (absorbant)
12-30% stearyl alcohol (main wax component)
0.5-4% hydrogenated castor oil (subordinate wax)
0.05-30% aluminum salt in the form of salt and encapsulated salt A second preferred embodiment of the invention is where the microcapsules ar incorporated into a roll-on antiperspirant deodorant. Roll-ons are generally liquid and comprise a vehicle into which the antiperspirant salts and other constituents are incorporated. In the preferred embodiment of the invention the roll-on comprises a number of desireable constitutents such as drying agents or enhancers, preservatives, suspending agents, whitening agents, and so on.

A drying enhancer is a material which enables the roll-on to dry more quickly. Generally an alcohol is suitable as a drying enhancer and a $C_{1-3}$ alcohol such as isopropyl alcohol, ethanol, SD alcohol 40-B, or any SD alcohol is suitable If the alcohol is included in the composition a range of 1-10% is suggested.

Suitable preservatives are those mentioned previously. If a preservative is included in the composition, a range of 0.1-0.6% is preferred.

A suspending agent aids in the suspension of the microcapsules and antiperspirant salts. Suitable suspension agents are mentioned above. A range of 1-5% is suggested.

The preferred roll-on composition comprises:
0.01-50% antiperspirant salt comprising 0.01-10% microcapsules and the remainder unencapsulated salt
10-70% silicone
1-5.0% silica (suspending agent)
0.001-5.0% quaternium 18 hectorite (suspending agent)

Another preferred roll on formulation contains, in addition to the above ingredients, 1-10% SD Alcohol 40-B (drying enhancer).

The microcapsules of the invention may also be incorporated into cream vehicles. Many types of creams are suitable including silicone based creams comprising about 10-60% silicone, 1-20% oils, and 1-20% emulsifiers and other optional ingredients such as humectants, silicone, waxes, etc. Water in oil or oil in water emulsions are also desireable. Such formulations comprise about 10-60% water, 40-90% oil, and may contain one or more of a humectant, silicone, wax, etc.

The microcapsules may be incorporated into an aerosol formulation. Traditional aerosols comprise a propellant in addition to other ingredients such as humectants, suspending agents, wetting agents, etc. Generally an aerosol containing 10-80% propellant is suggested with one or more of a humectant, suspending agent, wetting agent, fragrance, and so on in cosmetically acceptable amounts previously herein.

The microcapsules of the invention may also be incorporated into gels. Suitable gels comprise about 10-70% water, 1-10% gum and a variety of optional constituents such as humectants, emollients, fragrance, in amounts set forth herein.

The microcapsules of the invention may also be incorporated into a pump spray formulation. Suitable pump spray formulations comprise 10-70% silicone, 0.01-3% suspending agent; or 10-70% water, 1-20% alcohol, and 0.01-5% suspending agent.

The microcapsules of the invention may also be impregnated into sponges or pads. The pads are then used to apply the antiperspirant vehicle containing the microcapsules to the desired area.

The above antiperspirant/deodorant formulations provide excellent antiperspirant activity. The presence of the microcapsules containing the antiperspirant salts allows for time release of the salts. The bioadhesive adheres the microcapsules to the skin so they are not washed away with perspiration.

The invention will described in connection with the following examples which are set forth for the purpose of illustration only.

EXAMPLE 1

Two hundred ten grams of paraffin wax (Boler 1426, Boler Petroleum Co., Wayne PA) was melted in a glass beaker. Aluminum zirconium tetrchlorohydrex gly powder (90 g.) was emulsified into the molten wax. This emulsion was maintained at 200o F and was then fed into the center of a disk rotating at 9200 rpm. The emulsion formed a film on the disk which broke up into small droplets at the periphery of the disk due to centrifugal force. The molten droplets were solidified by cool air prior to collection on paper. The microspheres of the antiperspirant salt dispersed in the wax had an average diameter of 17 micrometers.

EXAMPLE 2

Microspheres of the aluminum zirconium tetrachlorohydrex gly powder in polyethylene (Polywax 500, Petrolite Corporation, Tulsa, OK) were prepared in a similar manner to Example 1. The aluminum zirconium tetrachlorohydrex gly (30 g.) was emulsified in the molten polyethylene (270 g.). The emulsion was maintained at 225° F. and fed into the center of a disk rotating at 9800 rpm. The microspheres had an average diameter of 19 micrometers.

EXAMPLE 3

Microspheres of the aluminum zirconium tetrachlorohydrex gly powder in partially hydrogenated cottonseed oil (Capital City Products Co. Columbus, OH) were prepared as described in Example 1. The powder (90 g.) was emulsified in the molten, partially hydrogenated cottonseed oil (210 g.). The emulsion was maintained at 190° F. and fed into the center of a disk rotating at 9200 rpm. The microspheres had an average diameter of 20 micrometers.

EXAMPLE 4

Microspheres of aluminum dichlorohydrate in polyvinylalcohol (Mowiol 3-83, American Hoechst Corp, Somerville, NJ) were prepared using a spray drying method. The polyvinyl alcohol (75 g.) was dissolved in deionized water (1425 g.) A 46% solution of aluminum dichlorohydrate in water (165 g.) was then added to the polyvinyl alcohol solution. The solution was then pumped, using a peristaltic pump, at a rate of 30 g/min. to a two fluid nozzle (Spraying Systems Fluid Cap 60100 with a 120 Air Cap) in the center of a spray dryer. A 40 psig air stream atomized the solution into small droplets which were dried by a heated countercurrent air stream at about 179° C. The dried product was transported by the air stream to a cyclone for collection. The microspheres prepared for this example averaged 10 micrometers in diameter.

EXAMPLE 5

Microspheres of aluminum tetraohlorohydrex gly in hydroxypropylmethylcellulose phthalate (HPMCP 55, Biddle Sawyer Corp., New York, NY) were prepared using a similar spray drying method. The hydroxypropylmethylcellulose phthalate (50 g.) was dissolved in acetone (450 g.). The aluminum zirconium tetrachlorohydrex gly powder (50 g.) was dispersed in the polymer solution. This dispersion was pumped using a peristaltic pump at a rate of 15 g/min to the two fluid nozzle described in Example 4, which is located in the center of the spray dryer. A 30 psig air stream atomized the dispersion into small droplets which were dried by an ambient temperature countercurrent air stream. The dried product collected in the cyclone had an average diameter of 12 micrometers.

EXAMPLE 6

Microspheres of aluminum tetrachlorohydrex gly in an acrylic resin (Elvacite 2008, Dupont Company, Wilmington DE) were prepared using the same spray drying method in Example 5. The acrylic resin (50 g.) was dissolved in toluene (200 g.). The antiperspirant salt powder (50 g.) was dispersed in the polymer solution. The dried product had an average diameter of 19 micrometers.

EXAMPLE 7

Microspheres of aluminum zirconium tetrachlorohydrex gly powder in a partially hydrogenated cottonseed oil (Sterotex K Capital City Products Co. Columbus, OH) with a bioadhesive, polyvinylalcohol, in the shell were prepared using the rotating disk method. The partially hydrogenated cottonseed oil (66.5 g.) was melted in a beaker. The polyvinylalcohol (Airvol 205S, Air Products and Chemicals, Co., Allentown, PA) (3.5 g.) and the antiperspirant salt (30 g.) were emulsified in the molten fat with a sonifier. The emulsion was maintained at 300° F. and fed to the oentez of a disk rotating at 9500 rpm. The product was cooled by air and collected on paper.

EXAMPLE 8

Microspheres of the aluminum zirconium tetrachlorohydrex gly powder in a paraffin wax (Boler 1014) with a bioadhesive in the shell were also prepared using the same rotating disk method described in Example 7. The bioadhesive, gum acacia, (1.5 g.), and the antiperspirant salt (25 g.) were emulsified using a sonifier, into the molten wax (73.5 g.)

EXAMPLE 9

Microspheres of the aluminum zirconium tetrachlorohydrex gly powder in an ozokerite wax (Ross Ozokerite Wax 871, Frank B. Ross, Jersey City, NJ) with a bioadhesive, xanthan gum, dispersed in the shell were prepared as described in Example 7. The xanthan gum, Rhodigel EZ (3.75 g.) and antiperspirant salt (25 g.) were emulsified using a sonifier into the molten wax. (71.25g).

EXAMPLE 10

Microspheres of the antiperspirant salt of Example 1 are coated with a bioadhesive outer coating such as sodium carboxymethylcellulose (Cellulose Gum 7L2, Aqualon Co., Wilmington, DE) by dissolving 5 grams of the bioadhesive in deionized water (395 g.). The microspheres (100 grams) are dispersed into the solution and spray dried as in Example 4.

EXAMPLE 11

Microspheres of the antiperspirant salt of Example 2 are coated with 5 grams of bioadhesive methylcellulose (Methocel A5, Dow Chemical Co., Midland, MI). The methylcellulose is dissolved in a combination of dichloromethane (316 g.) and ethanol (79 g.) About 100 g. of microcapsules are dispersed in the methylcellulose solution prior to feeding the solution to the center of a rotating disk. The droplets formed at the edge of the disk are solidified by evaporation of the solvent prior to collection on paper.

EXAMPLE 12

A dry roll of antiperspirant was made as follows:

|  | w/w % |
|---|---|
| Cyclomethicone | 59.00 |
| AP salt + Encap AP salt* | 30.00 |
| Dimethicone | 5.00 |
| SD alcohol 40-B | 3.00 |
| Silica | 1.25 |
| Quaternium-18 Hectorite | 1.25 |
| Fragrance | 0.50 |

*unencapsulated antiperspirant salt in combination with encapsulated anti-perspirant salt

EXAMPLE 13

A classic wet roll on was prepared as follows:

|  | w/w % |
|---|---|
| Magnesium aluminum silicate | 2.00 |
| Glyceryl stearate | 3.75 |
| Laureth 23 | 2.00 |
| Laureth 4 | 2.00 |
| Lapyrium chloride | 3.00. |
| AP salt + Encap AP salt | 30.00 |
| EDTA | 0.25 |
| Water | 57.00 |

EXAMPLE 14

A dry aerosol concentrate was made as follows:

|  | w/w % |
|---|---|
| Cyclomethicone | 28.00 |
| Isopropyl palmitate | 8.00 |
| Quaternium-18 hectorite | 2.00 |
| Propylene carbonate | 1.00 |
| Aluminum chlorohydrate + Encap aluminum chlorohydrate | 60.00 |
| Fragrance | 1.00 |
| Propellant/concentrate ratio = 80/20 | |

EXAMPLE 15

A silicone antiperspirant stick was made as follows:

| | w/w % |
|---|---|
| Cyclomethicone | 60.00 |
| Silica | 1.00 |
| Talc | 2.00 |
| Stearyl alcohol | 20.00 |
| Hydrogenated castor oil | 3.00 |
| PEG-8 distearate | 3.00 |
| AP salt + Encap AP salt | 30.00 |
| Fragrance | 1.00 |

EXAMPLE 16

An aqueous antiperspirant stick was made as follows:

| | w/w % |
|---|---|
| Propylene glycol | 35.50 |
| Lauryl lactate | 5.00 |
| Stearamide MEA | 22.00 |
| Simethicone | 1.00 |
| AP salt + Encap AP Salt | 30.00 |
| Glycine | 1.00 |
| Fragrance | 0.50 |
| Water | 5.00 |

EXAMPLE 17

A silicone base antiperspirant cream was made as follows:

| | w/w % |
|---|---|
| Hydrogenated castor oil | 4.00 |
| Glyceryl stearate | 5.50 |
| PEG-100 stearate | 2.00 |
| Cetyl acetate | 1.50 |
| Acetylated lanolin alcohol | 0.50 |
| Talc | 7.00 |
| AP salt + Encap AP salt | 30.00 |
| Cyclomethicone | 45.50 |
| Quaternium-18 hectorite | 1.00 |
| Silica | 1.00 |
| Fragrance | 1.00 |

EXAMPLE 18

An aqueous based antiperspirant cream was made as follows:

| | w/w % |
|---|---|
| Glycerin | 4.00 |
| Mineral oil | 4.00 |
| Dimethicone | 1.00 |
| Propylene glycol | 3.00 |
| Ceteareth alcohol | 6.00 |
| Ceteareth-20 | 3.00 |
| Paraffin | 9.00 |
| Water | 35.00 |
| Urea | 4.00 |
| AP salt + Encap AP salt | 30.00 |
| Fragrance | 1.00 |

EXAMPLE 19

A formulation suitable for a pump spray was made as follows:

| | w/w % |
|---|---|
| Cyclomethicone | 59.00 |

-continued

| | w/w % |
|---|---|
| AP salt + Encap AP salt* | 30.00 |
| Dimethicone | 5.00 |
| SD alcohol 40-B | 3.00 |
| Silica | 0.10 |
| Quaternium-18 Hectorite | 2.40 |
| Fragrance | 0.50 |

*free antiperspirant salt in combination with encapsulated anti-perspirant salt

While the invention has been described in connection with the preferred embodiment, it is not intended to limit the scope of the invention to the particular form set forth, but on the contrary, it is intended to cover such alternatives, modifications, and equivalents as may be included within the spirit and scope of the appended claims.

We claim:

1. An antiperspirant/deodorant composition containing microcapsules comprising 1-50% by weight of the microcapsule of one or more antiperspirant salts encapsulated within a shell wall comprising 50-95% by weight of the microcapsule of a water soluble shell wall material which is susceptible to osmotic, enzymatic, or electrolytic degradation, and 1-30% by weight of the microcapsule of a bioadhesive which is either a component of the shell wall or is coated on the surface thereof and causes the microcapsule to adhere to the skin surface.

2. The composition of claim 1 wherein the microcapsule is 1-75 microns in diameter.

3. The composition of claim 2 wherein the microcapsule is 10-60 micrometers in diameter.

4. The composition of claim 3 wherein the shell wall is comprised of an ingredient selected from the group consisting of polyvinylpyrrolidone, acrylic acid resin, chitosan glutamate, cellulose, dextran, modified food starch, polyvinylalcohol, glycerin, sorbitol, maltodextrin, corn syrup solids, sodium alginate, carrageenan, xanthan gum, ozokerite wax, polyethylene oxide, agarose, ethylene vinyl acetate copolymer, hydroxypropylcellulose, hydroxypropylmethylcellulose, hydroxypropylmethylcellulose phthalate, polyvinyl chloride, polystyrene, partially hydrogenated soybean oil, cottonseed oil, hydrogenated vegetable, oil, microcrystalline wax, beeswax, polyethylene, shellac wax, paraffin, natural waxes, synthetic waxes, or mixtures thereof.

5. The composition of claim 4 wherein the bioadhesive is an ingredient selected from the group consisting of sodium carboxymethyl cellulose, polyacrylic acid, tragacanth, polymethyl vinyl ether/maleric anhydride copolymer, polyethylene oxide, methylcellulose, karya gum, methylethylcellulose, soluble starch, geletan, pectin, polyvinyl alcohol, polyhydroxymethacrylate, hydroxypropyl cellulose, carbomers, chitin, gum acacia, xanthan gum, or mixtures thereof.

6. The composition of claim 5 wherein the antiperspirant salt is selected from the group consisting of aluminum bromohydrate, aluminum chlorhydrates, aluminum chlorohydrex propylene glycol, aluminum dichlorohydrex gly propylene glycol, aluminum sesquichlorohydrex propylene glycol, aluminum chlorohydrex polyethylene glycol, aluminum dichlorohydrex polyethylene glycol, aluminum sesquichlorohydrex polyethylene glycol, aluminum chloride, aluminum sulfate, aluminum zirconium chlorohydrates, aluminum zirconium trichlorohydrate, aluminum zirconium tetrachlorohydrate, aluminum zirconium pentachlorohydrate, aluminum zirconium octachlorohydrate, aluminum zirconium trichlorohydrex gly, aluminum zirconium tetrachlorohydrex gly, aluminum zirconium pentachlorohydrex gly, aluminum zirconium octachlorohydrex gly, buffered aluminum sulfate, potassium alum, sodium aluminum chlorohydroxy lactate, aluminum sesquichlorohydrates, sodium aluminum lactate, or mixtures thereof.

7. The composition of claim 1 where in the microcapsules the bioadhesive is a component of the shell wall.

8. The composition of claim 7 wherein the microcapsules comprises 1–20% bioadhesive, 1–50% antiperspirant salt, and 50–95% shell wall material.

9. The composition of claim 1 where in the microcapsules the bioadhesive is coated on the surface of the shell wall.

10. The composition of claim 1 wherein the antiperspirant/deodorant is a stick, roll-on, cream, pump spray, or gel.

11. The composition of claim 10 wherein the antiperspirant/deodorant is a stick.

12. The composition of claim 11 wherein the stick comprises 0.01–50% antiperspirant salt wherein the salt component is selected from the group consisting of 1–50% microcapsules and a mixture of 1–40% microcapsules and 1–50% free salt.

13. The composition of claim 12 further comprising 12–30% waxes and 10–70% silicone.

14. The composition of claim 13 further comprising an ingredient selected from the group consisting of a whitening agent, a suspending agent, a preservative, an absorbent, a wetting agent, or mixtures thereof.

15. The composition of claim 14 comprising 0.025–10% suspending agent, 0.1–3.0% whitening agent, 0.5–8% absorbant, or 0.01–0.060% preservative.

16. The composition of claim 15 wherein the wax is selected from the group consisting of stearyl alcohol, myristal alcohol, cetyl alcohol, tridecyl alcohol, microcrystalline, lanolin, paraffin, ozokerite, lanolin alcohol, hydrogenated lanolin, candelilla, cocoa butter, petrolatum, shellac, hydrogenated castor oil, spermaceti, bran wax, capok, bayberry, or mixtures thereof.

17. The composition of claim 16 wherein the whitening agent is selected from the group consisting of titanium dioxide, talc, mica, silicates, zinc oxide, or mixtures thereof.

18. The composition of claim 17 wherein the suspending agent is selected from the group consisting of silica, magnesium silicate, aluminum silicate, veegum, kaolin, or mixtures thereof.

19. The composition of claim 18 comprising:
10–70% silicone
0.1–3.0% titanium dioxide,
0.025–10% silica
0.5–3% talc,
12–30% stearyl alcohol,
0.5–4% hydrogenated castor oil,
1–50% aluminum salt which comprises up to 1–50% by weight microcapsules.

20. The composition of claim 10 which is a roll-on.

21. The composition of claim 20 comprising an ingredient selected from the group consisting of 1–10% drying enhancer, 0.1–0.6% preservative, 1–5% suspending agent or mixtures thereof.

22. The composition of claim 21 wherein the drying enhancer is a $C_{1-3}$ alcohol.

23. The composition of claim 22 wherein the suspending agent is selected from the group consisting of silica, magnesium silicate, aluminum silicate, veegum, kaolin, or mixtures thereof.

24. The composition of claim 23 comprising:
0.01–50% antiperspirant salt comprising 0.01–10% microcapsules and the remainder unencapsulated salt,
10–70% silicone,
1–5% silica,
0.001–5.0% quaternium 18 hectorite.

25. The composition of claim 24 additionally comprising 1–10% SD Alcohol 40-B.

26. The composition of claim 10 which is cream.

27. The composition of claim 26 comprising 10–60% water, 40–90% oil, 1–20% emulsifiers, or mixtures thereof.

28. The composition of claim 10 which is a pump spray.

29. The composition of claim 28 comprising an ingredient selected from the group consisting of 10–70% water, 1–20% alcohol, 10–70% silicone, 0.01–5% suspending agent, or mixtures thereof.

30. The composition of claim 10 which is a gel.

31. The composition of claim 30 comprising 10–70% water and 1–10% gum.

* * * * *